United States Patent
Pigg

(10) Patent No.: US 7,740,016 B1
(45) Date of Patent: *Jun. 22, 2010

(54) ANKLE AND FOOT IMMOBILIZER

(75) Inventor: Jimmy Pigg, Clifton, TN (US)

(73) Assignee: Modern Way Immobilizers, Inc., Clifton, TN (US)

( * ) Notice: Subject to any disclaimer, the term of this patent is extended or adjusted under 35 U.S.C. 154(b) by 261 days.

This patent is subject to a terminal disclaimer.

(21) Appl. No.: 11/169,214

(22) Filed: Jun. 28, 2005

(51) Int. Cl.
*A61B 19/00* (2006.01)
*A47B 13/00* (2006.01)
*G03B 42/02* (2006.01)

(52) U.S. Cl. .................. 128/869; 5/601; 378/177

(58) Field of Classification Search ............ 378/177, 378/178, 179, 180, 208, 209; 5/601, 624, 5/648, 650, 651; 128/882
See application file for complete search history.

(56) References Cited

U.S. PATENT DOCUMENTS

| | | | |
|---|---|---|---|
| 3,521,876 A * | 7/1970 | Smith | 5/601 |
| 3,783,863 A | 1/1974 | Kliever | 128/134 |
| 4,045,678 A * | 8/1977 | Rickard | 378/174 |
| 4,136,876 A * | 1/1979 | Kaplan | 273/144 B |
| 4,138,858 A * | 2/1979 | Petersen | 5/648 |
| 4,181,297 A | 1/1980 | Nichols | 269/328 |
| 4,232,681 A | 11/1980 | Tulaszewski | 128/653 |
| 4,310,935 A | 1/1982 | Stevens et al. | 5/80 |
| 4,320,749 A | 3/1982 | Highley | 128/83 |
| 4,323,080 A | 4/1982 | Melhart | 128/774 |
| 4,407,277 A | 10/1983 | Ellison | 128/82 |
| 4,457,302 A | 7/1984 | Caspari et al. | 128/133 |
| 4,612,661 A * | 9/1986 | Dallas | 378/77 |
| 4,615,516 A * | 10/1986 | Stulberg et al. | 5/650 |
| 4,827,496 A | 5/1989 | Cheney | 378/180 |
| 5,197,209 A * | 3/1993 | Rolland et al. | 36/118.9 |
| 5,462,551 A * | 10/1995 | Bailey et al. | 606/88 |
| 5,479,471 A * | 12/1995 | Buckland | 378/208 |
| 5,645,079 A | 7/1997 | Zahiri et al. | 128/846 |
| 5,716,334 A | 2/1998 | Wade | |
| 5,718,669 A | 2/1998 | Marble | 602/5 |
| 5,743,264 A | 4/1998 | Bonutti | 128/653.2 |
| 6,000,402 A | 12/1999 | Able | 128/869 |
| 6,012,456 A | 1/2000 | Schuerch | 128/869 |
| 6,234,173 B1 | 5/2001 | Hajianpour | 128/869 |
| 6,252,928 B1 | 6/2001 | MacKenzie | 378/54 |
| 6,254,561 B1 | 7/2001 | Borden | 602/24 |
| 6,308,712 B1 | 10/2001 | Shaw | 128/869 |
| 6,452,999 B1 | 9/2002 | Maida | 378/20 |

* cited by examiner

*Primary Examiner*—Patricia Bianco
*Assistant Examiner*—Tarla R Patel
(74) *Attorney, Agent, or Firm*—Waddey & Patterson, P.C.; Phillip E. Walker

(57) ABSTRACT

The present invention discloses an ankle and foot immobilizer has a base, a spine perpendicular to the base, and a shoulder perpendicular to both the base and spine. A foot cover is rotatably attached to the shoulder and engageable to the foot so that the sole is either resting upon the base to obtain a top view of the foot or so that the sole is resting against the spine to obtain a side-view of the foot. A vertical leg support that is releasably attached to the spine is provided to secure the leg in a vertical fashion. A horizontal leg support that is releasably attached to the spine is provided to secure the leg in a horizontal fashion. The base can have a cassette holder to so that a separate cassette holder is not required. The immobilizer has an anchor that can be releasably secured to a standard x-ray table such as a suction cup.

1 Claim, 5 Drawing Sheets

ANKLE AND FOOT IMMOBILIZER

This application claims priority to co-pending U.S. application Ser. No. 10/292,240 filed Nov. 12, 2002.

BACKGROUND OF THE INVENTION

The present invention relates generally to x-ray immobilization system and more particularly, to an ankle and foot immobilizer.

It will be appreciated by those of ordinary skill in the art for x-rays to be clearer, objects being x-ray needs to be still and immobilized. This is especially true when dealing with appendages that are injured and can sometimes not be held in place by the user. Some times the angles at which the foot or ankle is to be x-rayed are difficult to achieve if the foot or ankle is injured. Any type of vibration can adversely effect the x-ray. There have been several attempts to immobilize a lower appendage in x-rays.

U.S. Pat. No. 3,521,876 discloses a foot immobilizer. However, the piece of equipment is very bulky. Further, the Smith patent can only be used with the patient in the reclined position. Therefore, a foot X-ray can not be taken looking at the top of the foot. A different immobilizer must be used. The same limitation is found in U.S. Pat. Nos. 4,232,681; 4,310,935; 4,827,496; 5,645,079; 5,716,334; 5,743,264

U.S. Pat. No. 4,320,749 is a boot that straps onto the foot and ankle to determine whether an anterior talo fibular ligament has been ruptured. The apparatus does not allow the users foot to be examined for a side view.

U.S. Pat. Nos. 6,234,173 and 6,252,928 disclose even bulkier systems for securing a foot or ankle during an x-ray. These patents along with U.S. Pat. No. 5,743,264 are a part of an over-all x-ray table. U.S. Pat. No. 6,234,173 allows X-raying only the top of the foot.

U.S. Pat. No. 5,716,334 discloses a very simple system for immobilizing an ankle. Unfortunately, this does not provide for multiple angles. Instead, it appears to provide a top down view. Further, this is more intended to act as a means for drainage and immobilization not necessarily during x-rays.

U.S. Pat. No. 5,479,471 is another immobilization system. However, it does not appear to be able to immobilize a foot at different angles. Further, the apparatus is strapped onto the foot in such a way that slippage of the awkward boot could further damage the foot or ankle.

U.S. Pat. No. 4,323,080 is an ankle stress machine. This ankle stress machine also has a built in radiation system. That is it provides measurement at various angles. However, the multiple mechanisms would interfere with an external radiation source. Further, the top X-ray of the foot is not possible.

What is needed, then, is an ankle and foot immobilizer. This ankle and foot immobilizer must be capable of immobilizing a foot so that an x-ray can be taken of either side of the foot and of the top of the foot. This needed system must be basically one piece but transformable to allow the versatility to measure both the top view and either side view. This needed system must also be capable of providing a cassette holder. This needed system must be capable of being secured onto a standard x-ray table. This needed system must be capable of securing different sizes of feet. This needed immobilizer is currently lacking in the prior art.

SUMMARY OF THE INVENTION

The present invention discloses an ankle and foot immobilizer has a base, a spine perpendicular to the base, and a shoulder perpendicular to both the base and spine. A foot cover is rotatably attached to the shoulder and engageable to the foot so that the sole is either resting upon the base to obtain a top view of the foot or so that the sole is resting against the spine to obtain a side-view of the foot. A vertical leg support that is releasably attached to the spine is provided to secure the leg in a vertical fashion. A horizontal leg support that is releasably attached to the spine is provided to secure the leg in a horizontal fashion. The base can have a cassette holder so that a separate cassette holder is not required. The immobilizer has an anchor that can be releasably secured to a standard x-ray table such as a suction cup.

Accordingly, one object of the present invention is to provide the ankle and foot immobilizer.

Another object of the present invention is to provide an ankle and foot immobilizer that can be used to secure the foot to take either a top view of the foot or a side view of either side of the ankle.

Another object of the present invention is to provide an immobilizer that can be used on any standard table such as an x-ray table.

Another object of the present invention is to provide an immobilizer that provides its own cassette holder.

Still yet another object of the present invention is to provide a system that is x-ray translucent and easy to disinfect.

Still another object of the present invention is to provide an immobilizer that holds the foot in place thereby decreasing the need to retake X-rays blurred by movement.

Yet another object of the present invention is provide an immobilizer that allows the X-ray technician to take an accurate X-ray without having to manually immobilize the foot and having to be exposed to the radiation.

DESCRIPTION OF THE PREFERRED EMBODIMENTS

Figure 1:
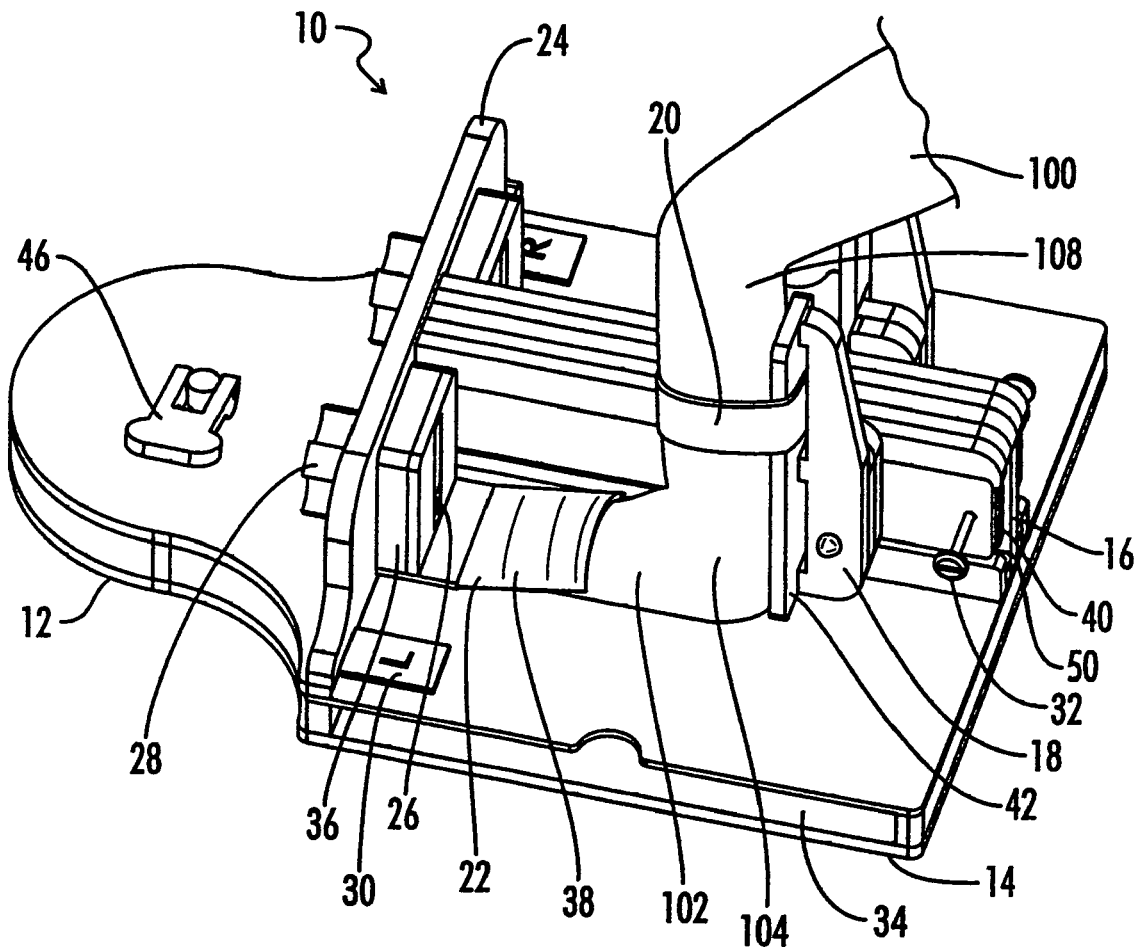
FIG. 1 is a perspective view showing the ankle and foot immobilizer being used by an individual.
Figure 2:
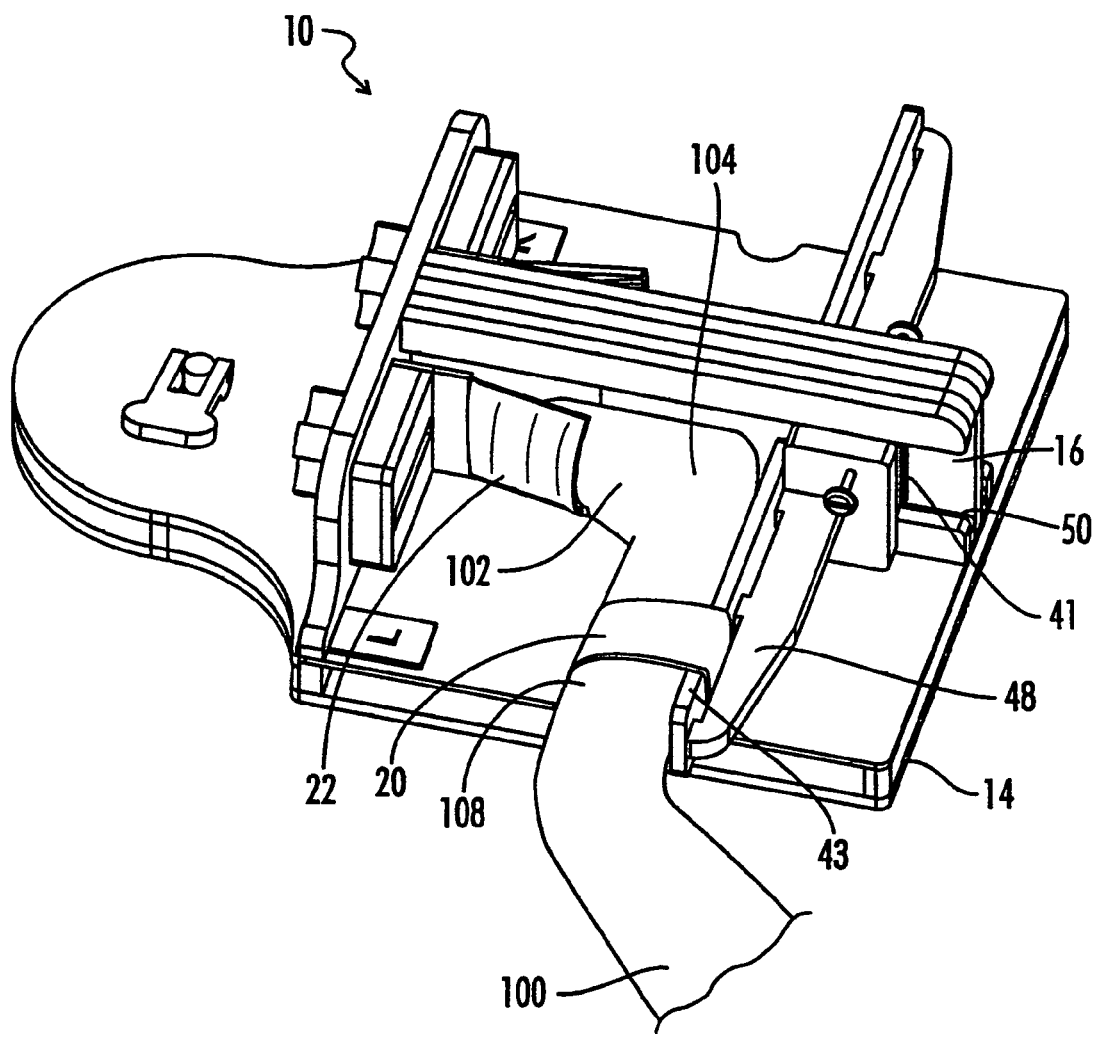
FIG. 2 is a perspective of the ankle and foot immobilizer of the present invention showing the foot aligned in a position to take the side x-ray of a foot.
Figure 3:
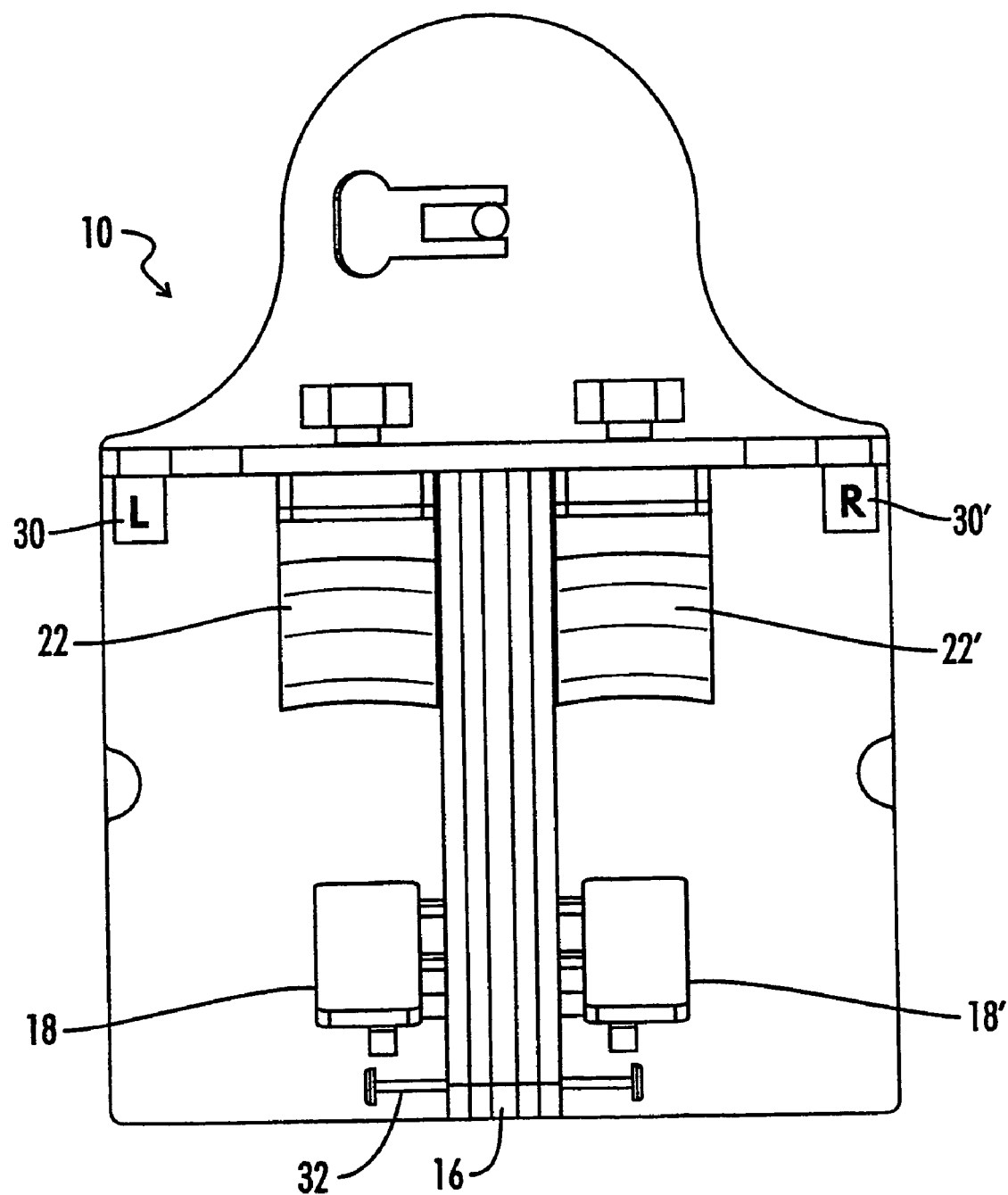
FIG. 3 is a plan view of the infant immobilizer of the present invention.

Referring now to FIG. 1 there is shown generally at 10 the ankle and foot immobilizer of the present invention Ankle and foot immobilizer 10 is provided with anchor 12 so that it can be secured on any existing surface such as an existing x-ray table. In a preferred embodiment, anchor 12 is a suction cup 44 shown in FIG. 5 that can be secured or released using lever 46. Anchor 12 is attached to base 14. In a preferred embodiment, base 14 is bisected by spine 16. Spine 16 rises substantially perpendicularly from base 14. Attached perpendicularly to base 14 there is shoulder 24. In the preferred embodiment, spine 16 is perpendicularly secured to shoulder 24 and bisects shoulder 24. Base 14 is preferably provided with a cavity which acts as cassette holder 34. This allows cassette film cartridge to be easily slid in and out of immobilizer 10. In the preferred embodiment, the immobilizer 10 is provided with foot cover 22 and vertical leg support 18. In the preferred embodiment, foot cover 22 comprises foot bracket 36 that is attached foot shield 38. In the preferred embodiment, foot bracket 36 is rotatably attached to shoulder 24 to allow the foot 102 of the user 100 to be engaged in such a way as to provide a top x-ray of foot 102 as shown in FIG. 1 or a side x-ray of foot 102 as shown in FIG. 2. In the preferred embodiment, foot bracket 36 is secured to shoulder 24 using shoulder screw 26 that is tightened and released by shoulder knob 28. As seen in FIG. 3, a second foot cover 22' can also be provided. Indicator 30 is provided to show whether it is the left foot or the right foot. Therefore, indicator 30 has either an "L" or an "R."

Referring still to FIG. 1, in the preferred embodiment, immobilizer 10 is also provided with vertical leg support 18 engaged the leg 108 of the user 100. In the preferred embodiment, leg support 18 has vertical leg bracket 40 that releasably and slidably attaches to track 50 of spine 16. Vertical leg bracket 40 is attached to vertical leg shield 42. Strap 20 can be provided to more adequately secure leg 108 to leg support 18. In the preferred embodiment, a vertical leg bracket 40 is releasably and slidably attached to track 50 spine 16 and kept from moving using spine screw 32 which is a set screw. In the preferred embodiment, vertical leg support 18 is rotatably secured to vertical leg bracket 40 to allow the angle of leg 108 to be varied to get a better view of the area to be X-rayed.

Referring now to FIG. 2, there is shown generally at 10 the ankle and foot immobilizer of the present invention showing leg 108 in a different orientation. In this instance, leg 108 is placed substantially parallel and on top of base 14 so that the sole of the foot 102 is substantially against spine 16. In this orientation, the side of user's foot 102 can be x-rayed. Strap 20 allows leg 108 to be held against horizontal leg support 48. Foot 102 is held in place by foot cover 22. It should be realized that the view shown in FIG. 2 allows either the inside ankle 104 or outside ankle 104 of user 100 to be x-rayed. In this embodiment, horizontal leg support 48 has horizontal leg bracket 41 secured to horizontal leg shield 43. Horizontal leg bracket is slidably and releasably attached to track 50 of spine 16 thereby allowing differently-sized feet to be X-rayed. Track 50 runs along spine 16 substantially parallel to base 14.

Referring now to FIG. 3, there is shown generally at 10 still another view of the immobilizer of the present invention. This can be seen, immobilizer 10 has a left side and a right side. Therefore, in the preferred embodiment first foot cover 22 and second foot cover 22' are provided. Likewise, first vertical leg support 18 and second vertical leg support 18' are provided. First or left indicator 30 and second or right indicator 30' are provided. As can be seen from this view, vertical leg supports 18 and 18' can be angled forward and backwards along spine 16 at different angles of orientation of a user's leg to better show of the user's foot. In a preferred embodiment, vertical leg support 18 is attached to track 50 of spine 16 and held in place using spine screw 32 as a set screw. In an alternative embodiment, several holes are actually placed into spine 16 to allow leg support 18 to move toward and/or away from shoulder 24 to vary the size of the foot to be immobilized.

Figure 4:
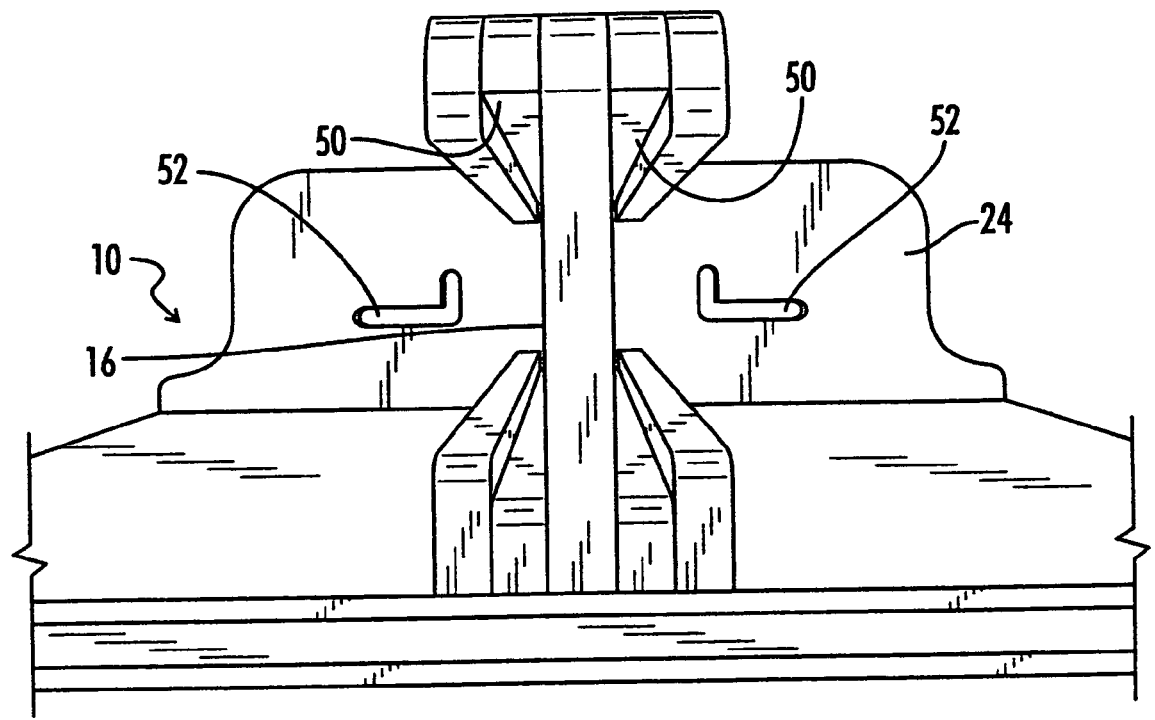
FIG. 4 is an end view of the infant immobilizer of the present invention.

Referring now to FIG. 4 there is shown an end view of the immobilizer 10 of the present invention. This view better shows track 50 running along each side of spine 16. Additionally, FIG. 4 also shows how foot cover (22 in FIG. 1) can be moved about shoulder 24. In the preferred embodiment, holes 52 are placed in shoulder 24 on either or bother sides of spine 16. Shoulder screw (26 in FIG. 1) passes through hole 52 and is received by foot bracket (36 in FIG. 1). Hole 52 is preferably L-shaped to allow foot cover 22 to be moved up and away from spine 16 to accommodate bigger feet. However, any shaped holes can be used including long angular hole that rises as it moves away from spine 16.

Figure 5:
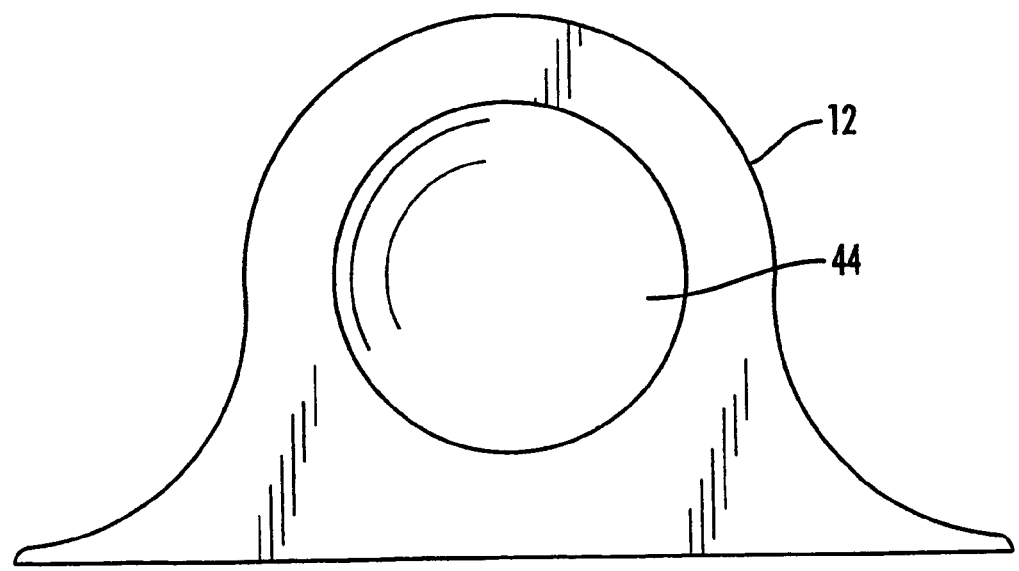
FIG. 5 is a view of the underside of the anchor.

Referring now to FIG. 5 there is shown generally at 12, the underside of the anchor of the present invention. Anchor 12 uses suction cup 44 activated by lever (46 in FIG. 1) to secure and release cup 44.

Figure 6:
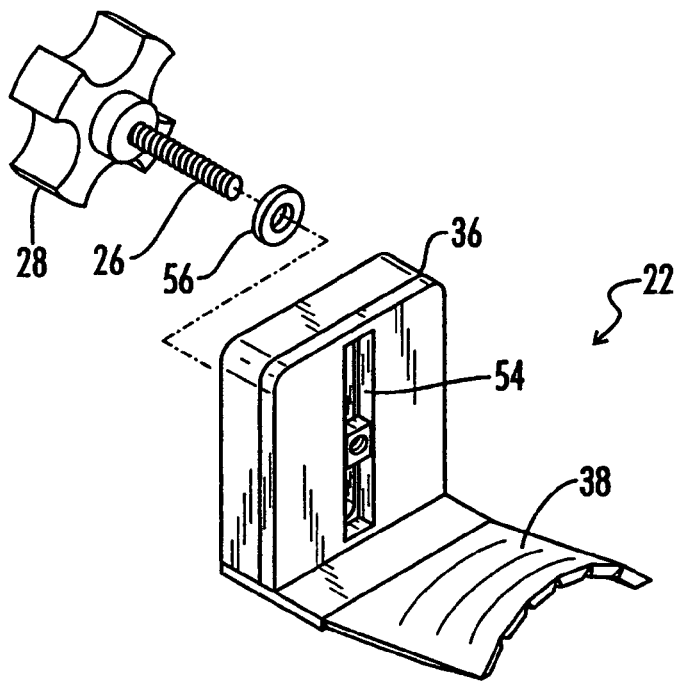
FIG. 6 is a perspective view of the foot cover of the present invention.

Referring now to FIG. 6 there is shown generally at 22, the foot cover of the present invention. Foot cover 22 has foot bracket 36 connected to foot shield 38. In the preferred embodiment, foot bracket 36 has an elongated foot bracket hole 54 that allows the foot cover 22 to be adjusted vertically when used as shown in FIG. 1 and horizontally when used as shown in FIG. 2. Again, shoulder screw 26 adjusted by shoulder knob 28 is received by foot bracket 36. Shoulder knob 28 can be used to tension foot bracket 36. Washer 56 can also be provided.

Figure 7:
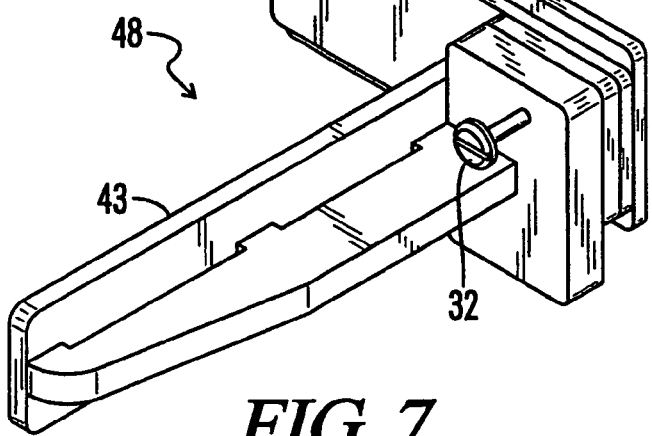
FIG. 7 is a perspective view of the horizontal leg support of the present invention.

Referring now to FIG. 7, there is shown generally at 48 the horizontal leg support of the present invention. As can be seen horizontal leg support 48 has horizontal leg bracket 41 adjoined to horizontal leg shield 43. As shown in FIGS. 1 and 7, horizontal leg bracket 41 slides along track 50 of spine 16 and in held in place by spine screw 32 which is used as a set screw. Holes can also be placed in spine 16.

Figure 8:
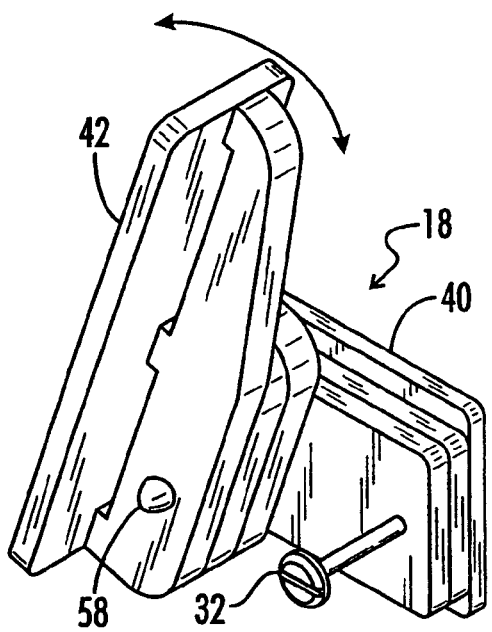
FIG. 8 is a perspective view of the vertical leg support of the present invention.

Referring now to FIG. 8, there is shown generally at 18 the vertical leg support of the present invention. This can be seen vertical leg support 18 has vertical leg bracket 40 adjoined to vertical leg shield 42 at pivot 58. Shoulder screw 26 acts as a set screw to hold vertical leg support 18 at a spot along track 50 along which support 18 slides. As also seen in FIG. 1, the vertical leg shield 42 of the vertical leg support 18 includes an open bottom to allow a foot 102 to engage the base 14.

The preferred embodiment of immobilizer has spine 16 secured to base 14. However, it should be understood that spine 16 could be releasably attached to base 14. Preferably, spine 16 is a unitary piece. However, it should be understood that spine 16 could be made of several pieces. Similarly, shoulder 24 could be removably attached to base 14 and/or made of multiple pieces.

Thus, although there have been described particular embodiments of the present invention of a new and useful Foot Immobilizer, it is not intended that such references be construed as limitations upon the scope of this invention except as set forth in the following claims.

What is claimed is:

1. An immobilizer for X-raying a leg or foot of a user, the foot having a sole, the immobilizer comprising:
   a base;
   a spine attached substantially perpendicularly to the base; and
   a vertical leg support releasably attached to the spine for engaging a leg of a user, the vertical leg support having an open bottom such that a major portion of the sole of the user is exposed and wherein the vertical leg support is releasably attachable at various points along the spine.

* * * * *